(12) United States Patent
Côté

(10) Patent No.: US 8,403,275 B2
(45) Date of Patent: Mar. 26, 2013

(54) MEDICAL SUPPORT SYSTEM

(75) Inventor: Jocelyn Côté, Montréal (CA)

(73) Assignee: FI2S (8043523 Canada Inc.), Boucherville (CA)

( * ) Notice: Subject to any disclaimer, the term of this patent is extended or adjusted under 35 U.S.C. 154(b) by 0 days.

(21) Appl. No.: 12/487,680

(22) Filed: Jun. 19, 2009

(65) Prior Publication Data

US 2009/0314906 A1    Dec. 24, 2009

Related U.S. Application Data

(63) Continuation of application No. PCT/CA2007/002349, filed on Dec. 21, 2007.

(60) Provisional application No. 60/871,157, filed on Dec. 21, 2006.

(51) Int. Cl.
*A47K 1/04* (2006.01)

(52) U.S. Cl. ............... 248/129; 248/281.11; 248/125.7; 248/122.1; 211/85.18; 280/79.3

(58) Field of Classification Search .......... 248/281.11, 248/125.8, 126, 127, 161, 411, 157, 176.1, 248/412, 125.1, 132, 129, 122.1, 125.7, 289.11, 248/121, 282.1; 211/85.18, 71.01, 207, 189, 211/196, 197, 205, 115, 166, 95; 280/79.3
See application file for complete search history.

(56) References Cited

U.S. PATENT DOCUMENTS

| | | | | |
|---|---|---|---|---|
| 1,782,660 A * | 11/1930 | Meyer | ........................... | 248/413 |
| 2,470,524 A * | 5/1949 | Scudder | ..................... | 248/122.1 |
| 3,516,425 A * | 6/1970 | Rigal | .............................. | 135/67 |
| 3,709,556 A * | 1/1973 | Allard et al. | ............... | 297/188.2 |
| 4,332,378 A | 6/1982 | Pryor | | |
| 4,431,206 A * | 2/1984 | Pryor | ......................... | 280/304.1 |
| 4,541,596 A | 9/1985 | Price | | |
| 4,596,484 A * | 6/1986 | Nakatani | ...................... | 403/104 |
| 4,673,154 A * | 6/1987 | Karapita | ...................... | 248/320 |
| 4,725,027 A * | 2/1988 | Bekanich | .................... | 248/125.8 |
| 4,744,690 A * | 5/1988 | Hsieh | ............................. | 403/104 |
| 4,761,092 A * | 8/1988 | Nakatani | ...................... | 403/104 |
| 4,807,837 A | 2/1989 | Gawlik et al. | | |
| 4,945,592 A | 8/1990 | Sims et al. | | |
| 4,993,683 A * | 2/1991 | Kreuzer | ....................... | 248/639 |
| 5,108,064 A * | 4/1992 | Kreuzer | ....................... | 248/327 |
| 5,135,191 A | 8/1992 | Schmuhl | | |
| 5,306,109 A | 4/1994 | Kreuzer et al. | | |
| 5,344,169 A * | 9/1994 | Pryor et al. | .................. | 280/79.3 |
| 5,421,548 A * | 6/1995 | Bennett et al. | ............... | 248/129 |
| 5,482,239 A * | 1/1996 | Smith | ....................... | 248/229.13 |
| 5,509,680 A * | 4/1996 | Scharf et al. | ............... | 280/304.1 |
| 5,556,065 A * | 9/1996 | Wadley | ......................... | 248/129 |

(Continued)

FOREIGN PATENT DOCUMENTS

| | | |
|---|---|---|
| CA | 2029492 | 5/1991 |
| WO | WO2005/037164 A2 | 4/2005 |

OTHER PUBLICATIONS

International Search Report, PCT/2007/002349, Feb. 11, 2008.

*Primary Examiner* — Kimberly Wood
(74) *Attorney, Agent, or Firm* — Norton Rose Canada LLP

(57) ABSTRACT

A support frame for supporting an intravenous bag and associated equipment, comprises a main pole adapted to be secured to a structure so as to be self-standing. A pivotable pole is adapted to support equipment associated with an intravenous bag. A pivot joint is provided between the main pole and the pivotable pole such that the pivotable pole rotates about the main pole. A rack is supported by the pivotable pole, the rack being adapted to support an intravenous bag.

11 Claims, 7 Drawing Sheets

U.S. PATENT DOCUMENTS

| | | | |
|---|---|---|---|
| 5,878,536 A * | 3/1999 | Demmitt et al. | 52/36.4 |
| 6,007,124 A | 12/1999 | Thies, Jr. | |
| 6,231,016 B1 * | 5/2001 | Slone | 248/200.1 |
| 6,390,311 B1 * | 5/2002 | Belokin | 211/204 |
| 6,725,483 B2 * | 4/2004 | Gallant et al. | 5/658 |
| 6,908,249 B2 * | 6/2005 | Tomm | 403/109.1 |
| 7,195,377 B2 * | 3/2007 | Tsai | 362/431 |
| 7,748,672 B2 * | 7/2010 | Walke | 248/207 |
| 2002/0011543 A1 | 1/2002 | Chinn et al. | |
| 2002/0162926 A1 * | 11/2002 | Nguyen | 248/229.25 |

* cited by examiner

MEDICAL SUPPORT SYSTEM

CROSS-REFERENCE TO RELATED APPLICATIONS

This patent application is a continuation of PCT Patent Application No. PCT/CA2007/002349, filed on Dec. 21, 2007, and claims priority on United States Provisional Patent Application No. 60/871,157, filed on Dec. 21, 2006.

BACKGROUND OF THE APPLICATION

1. Field of the Application

The present application relates to a medical support system for supporting intravenous bags and associated mechanical equipment.

2. Background Art

Solutions of nutritional fluids are often supplied to patients intravenously. In many instances, a stand supports a fluid bag adjacent to a patient, and mechanical apparatuses such as pumps and monitoring devices are optionally provided in association with the intravenous tubing while being supported by the stand. Intravenous bag stands are often provided with casters, in order to follow the patient in his/her displacements.

When patients in wheelchairs, hospital beds or carts are displaced while being fed by intravenous bags, a hospital attendant must ensure that the stand remains close to the patient, if the wheelchair, hospital bed or cart does not have a support for the stand. This results in the slow and awkward displacement of such patients. In some emergency instances, it is often required that more than one attendant be involved in the transfer of a patient.

U.S. Pat. No. 5,135,191, issued on Aug. 4, 1992 to Schmuhl, discloses a medical support system provided with casters. The support system has a telescopic pole supporting fluid bags and associated equipment. The pole has two different diameters at a bottom end thereof, so as to be fitted in wheelchairs, hospital beds and carts. A fixed brace is provided with a knob, and a rotation of the knob results in pressure threadingly applied to the pole, so as to lock the pole to the stand, wheelchair, hospital bed or cart.

One of the issues associated with such locking systems is that they are manipulated by a plurality of attendants. Accordingly, it has often occurred that stronger attendants tighten the knob with such force that other attendants loosen the knob.

Also, the pole supports intravenous bags and mechanical devices. Accordingly, the pole is quite heavy, rendering the action of transferring of the pole from stand to wheelchair/bed exclusive to some stronger attendants.

SUMMARY OF THE APPLICATION

It is therefore an aim of the present application to provide a medical support system that addresses issues associated with the prior art.

Therefore, in accordance with the present application, there is provided a support frame for supporting an intravenous bag and associated equipment, comprising: a main pole adapted to be secured to a structure so as to be self-standing; a pivotable pole adapted to support equipment associated with an intravenous bag; a pivot joint between the main pole and the pivotable pole such that the pivotable pole rotates about the main pole; and a rack supported by the pivotable pole, the rack being adapted to support an intravenous bag.

Further in accordance with the present application, there is provided a medical support system comprising the support frame; and a wall support mounted to a wall, the wall support releasably supporting the main pole of the support frame such that the support frame is mounted to the wall.

Still further in accordance with the present application, there is provided a method for displacing a support frame supporting an intravenous bag and associated equipment, comprising: providing a stand supporting the support frame; lowering a platform of the stand to engage the support frame on a wall support; and moving the stand away from the support frame thereon.

DESCRIPTION OF THE PREFERRED EMBODIMENTS

Figure 1:
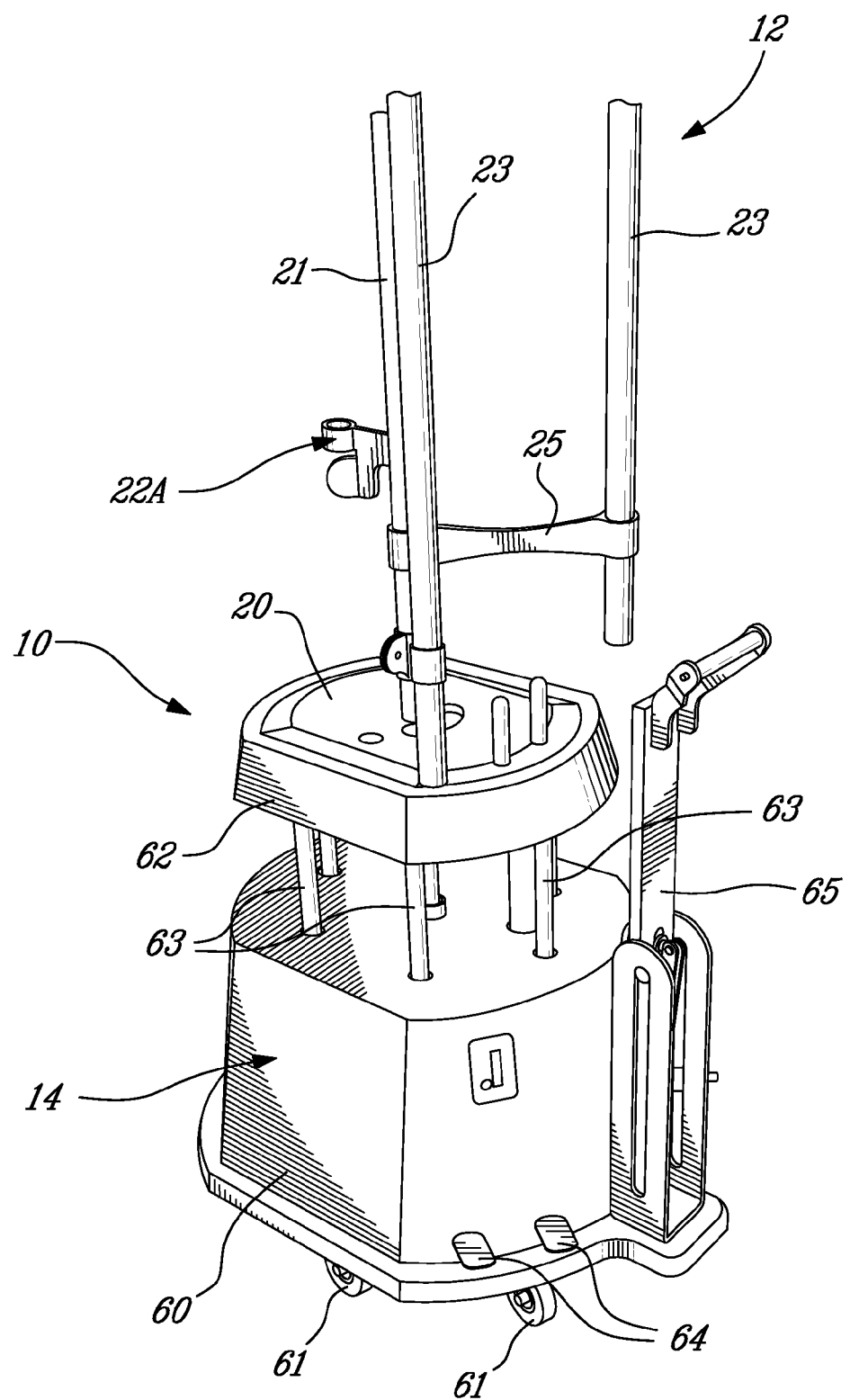
FIG. 1 is a perspective view of a medical support system constructed in accordance with a first embodiment of the present application.
Figure 3:
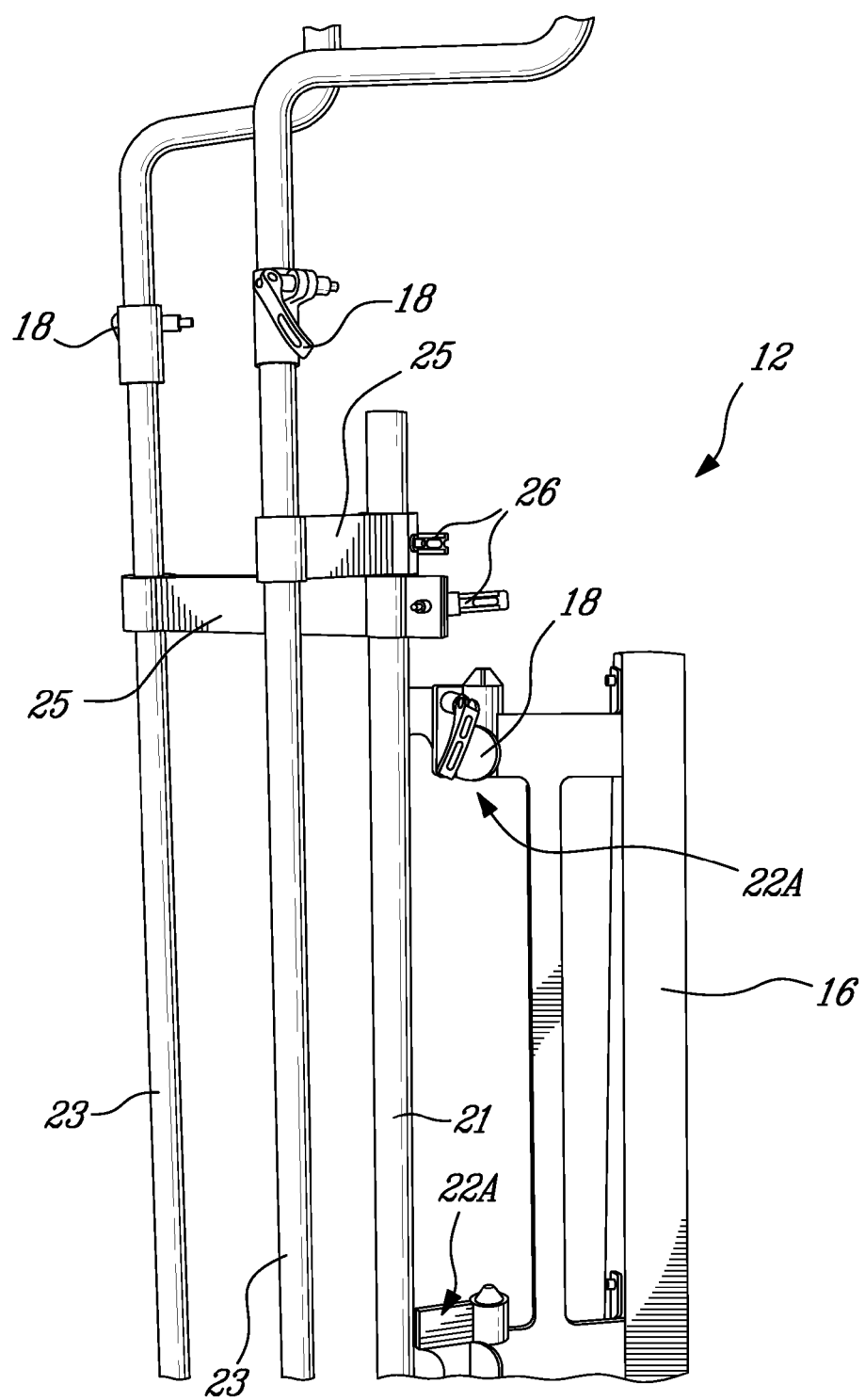
FIG. 3 is an enlarged perspective view of the support frame of FIG. 2, as mounted to a wall support.

Referring now to the drawings and, more particularly to FIG. 1, a medical support system in accordance with a first embodiment is generally shown at 10. The medical support system 10 has a support frame 12 and a wheeled stand 14. A wall support 16, as illustrated in FIG. 3, is part of the medical support system 10.

The support frame 12 is provided to support intravenous bags, as well as associated mechanical apparatuses, such as pumps (e.g., volumetric pumps) and monitoring devices.

The wheeled stand 14 is provided to support the support frame 12, and facilitate displacements thereof. The support frame 12 may be mounted directly onto a bed as well.

The wall support 16 is typically positioned adjacent to the patient's bed, and is provided to support the support frame 12. The wall support 16 may be provided with a railing system, so as to be displaceable within a room along a wall.

Referring to FIG. 1, connector mechanisms 18 are provided on the support frame 12, for the rapid connection/disconnection of components of the support frame 12.

Figure 2:
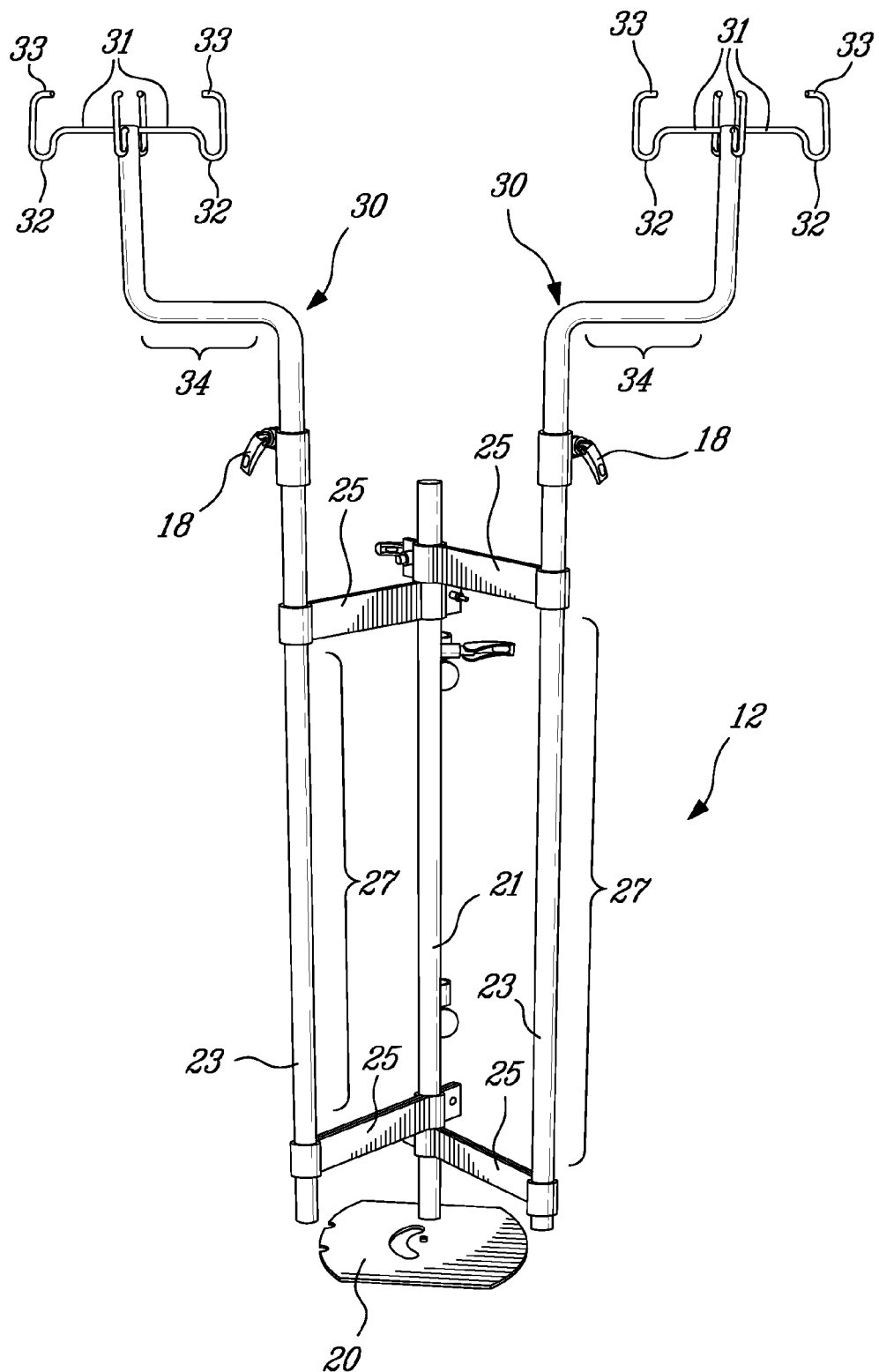
FIG. 2 is a perspective view of a support frame of the medical support system of FIG. 1.

Referring to FIG. 2, the support frame 12 is shown having a base plate 20. The base plate 20 is the interface between the support frame 12 and the wheeled stand 14. A main pole 21 projects upwardly from the base plate 20. As shown in FIG. 3, a pair of female connectors 22A (one shown) are spaced apart on the main pole 21, and are mated with corresponding male connectors of the wall support 16. A connector mechanism 18 is provided adjacent to one of the female connectors 22A to releasably lock the support frame 12 to the wall support 16.

Pivotable poles 23 are pivotally connected to the main pole 21, by way of pairs of parallel arms 25. Although the embodiment of FIGS. 1 and 2 involves a pair of the pivotable poles 23, it is contemplated to provide one or more of these poles 23 in the support frame 12. The pivotable poles 23 pivot about the main pole 21, and locking mechanisms 26 lock the pivotable poles 23 in selected positions.

Each of the poles 23 has a support length 27 (e.g., up to 70 inches in length)upon which mechanical apparatuses may be secured. As such apparatuses may be bulky, the pivoting motion of the poles 23 enables an attendant to optimize the space used by the support frame 12 in supporting the mechanical apparatuses.

Figure 4:
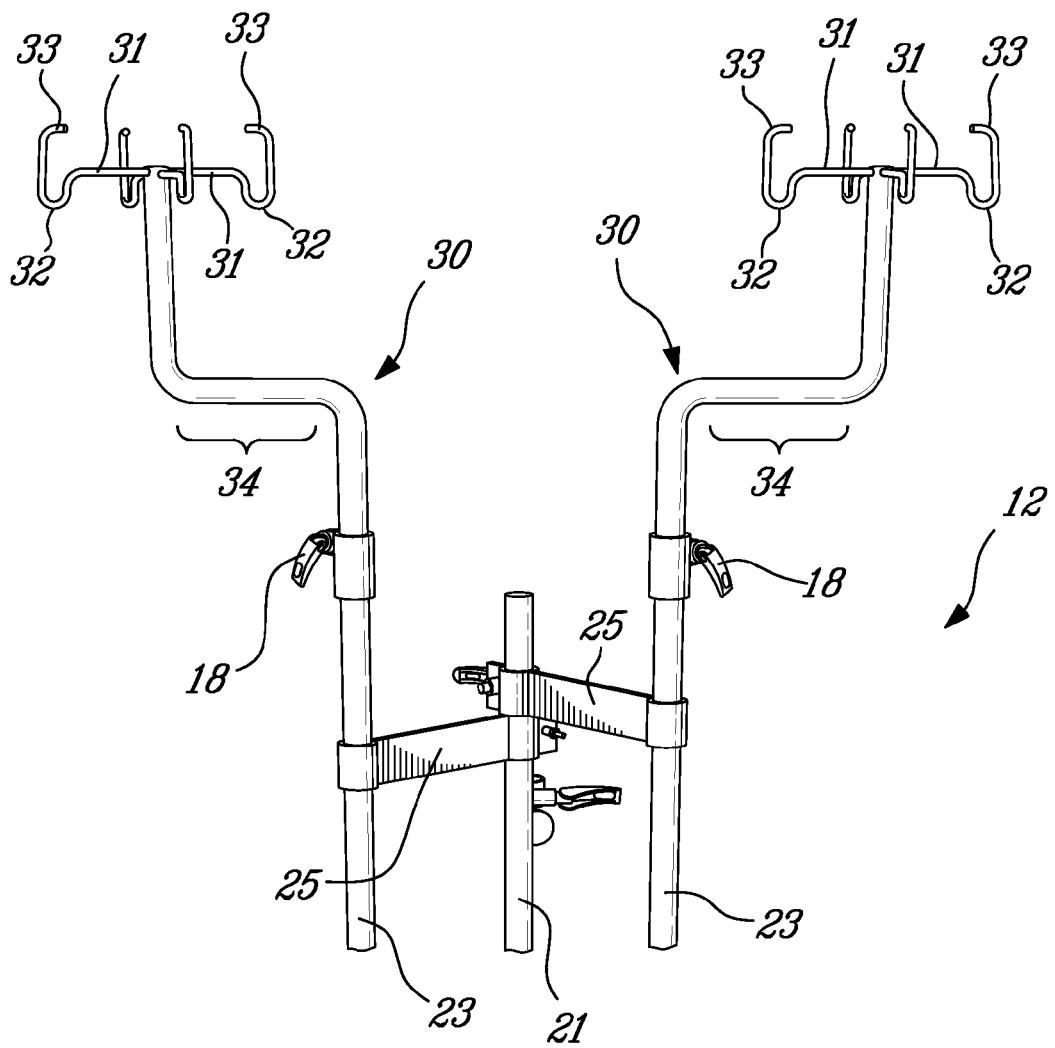
FIG. 4 is an enlarged perspective view of a rack of the support frame of FIG. 2.

Racks 30 are removably secured to a top end of the pivotable poles 23. As both the racks 30 are the same, only one of the racks 30 is now described. The rack 30 has fingers 31 provided to support the intravenous fluid bags (not shown). In the embodiment illustrated in FIG. 4, the rack 30 has four of the fingers 31. Each of the fingers 31 has a downwardly-oriented loop 32, as well as an inward tip 33. Accordingly, when a bag is hooked to one of the fingers 31, it will remain virtually captive by the combination of the downwardly oriented loop 32 and the inward tip 33.

The racks 30 are removably secured to the pivotable poles 23, by being telescopically retained therein by one of the connector mechanism 18. It is contemplated to insert a spring or like biasing member in the pivotable poles 23, to urge the rack 30 upward upon release of the locking mechanism from the connector mechanism 18, to facilitate removal of the rack 30 from the support frame 12.

An offset length 34 is optionally provided in the rack 30, to separate the bags supported by the rack 30 from the pivotable poles 23.

Figure 5:
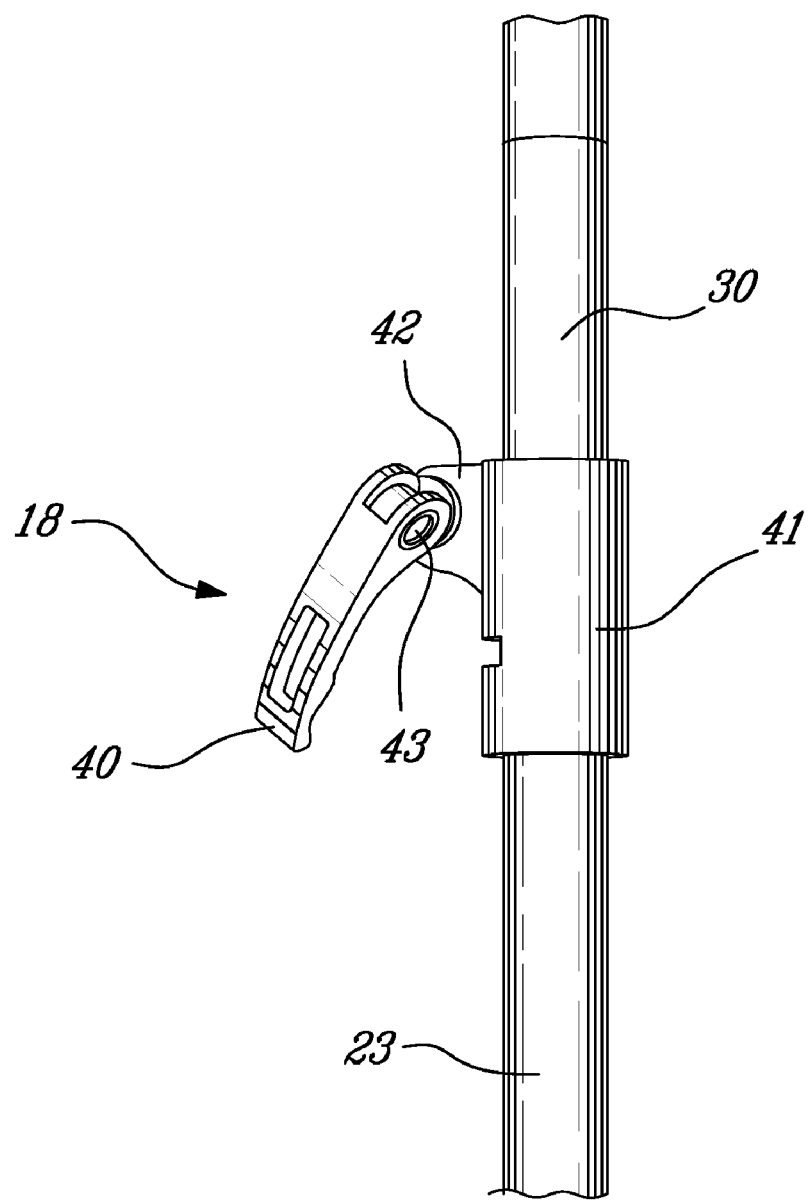
FIG. 5 is a perspective view of a connector mechanism as used on the support frame of FIG. 2.
Figure 6:
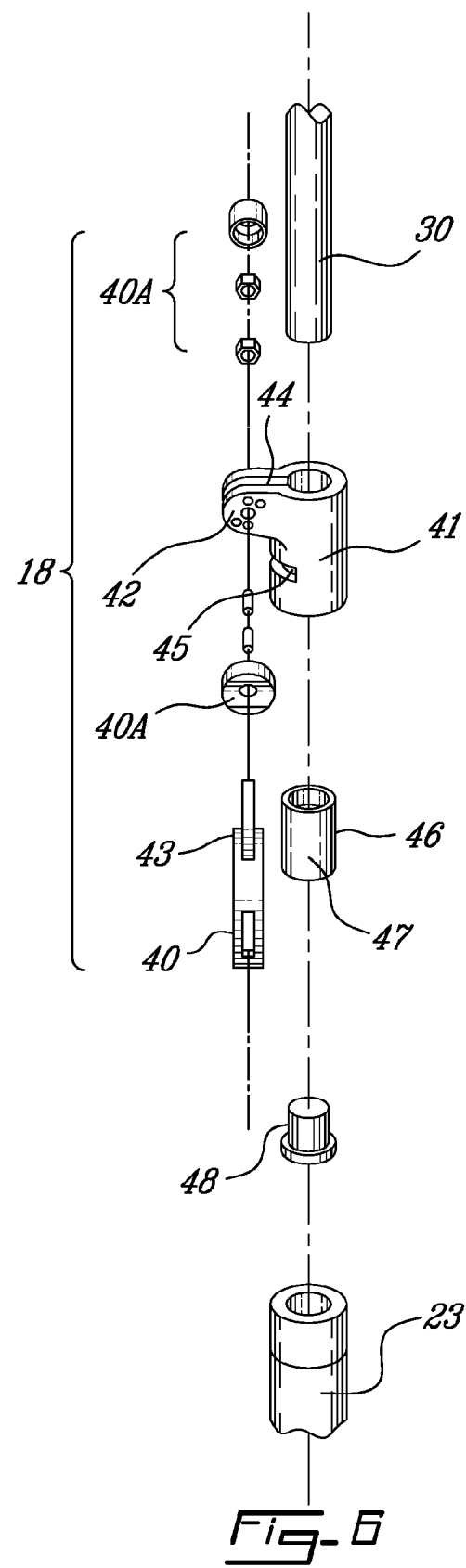
FIG. 6 is an exploded view of the connector mechanism of FIG. 5.

Referring concurrently to FIGS. 5 and 6, one of the connector mechanisms 18 is shown in greater detail. The connector mechanism 18 has a lever 40 mounted to an outer sleeve 41. The lever 40 is pivotally mounted to a connector end 42 of the sleeve 41, and incorporates locking nuts 40A. The lever 41 has a cam head 43, so as to exert pressure upon the connector end 42 in a locking motion thereof.

The connector end 42 defines a vertical gap 44, which gap 44 is reduced in width by the action of the cam head 43 of the lever 40. A bottom portion of the outer sleeve 41 is fixed to a top end of the pivotable pole 23. A horizontal gap 45, communicating with the vertical gap 44, ensures that the locking action of the lever 40 does not cause substantial pressure on the pivotable pole 23.

An inner sleeve 46 is enclosed in the outer sleeve 41, and is the interface between the rack 30 and the outer sleeve 41. The inner sleeve 46 has a vertical slit 47 that allows a change in inner diameter of the inner sleeve 46 in response to a locking action of the lever 40. Accordingly, the inner sleeve 46 holds the rack 30 captive until the lever 40 is actuated to release the rack 30. If the rack 30 is made of stainless steel, it is preferred to have the inner sleeve 46 made of a softer material, such as brass. A spring 48 biases the rack 30 upwardly to facilitate the removal of the rack 30 from the connector mechanism 18.

Figure 7:
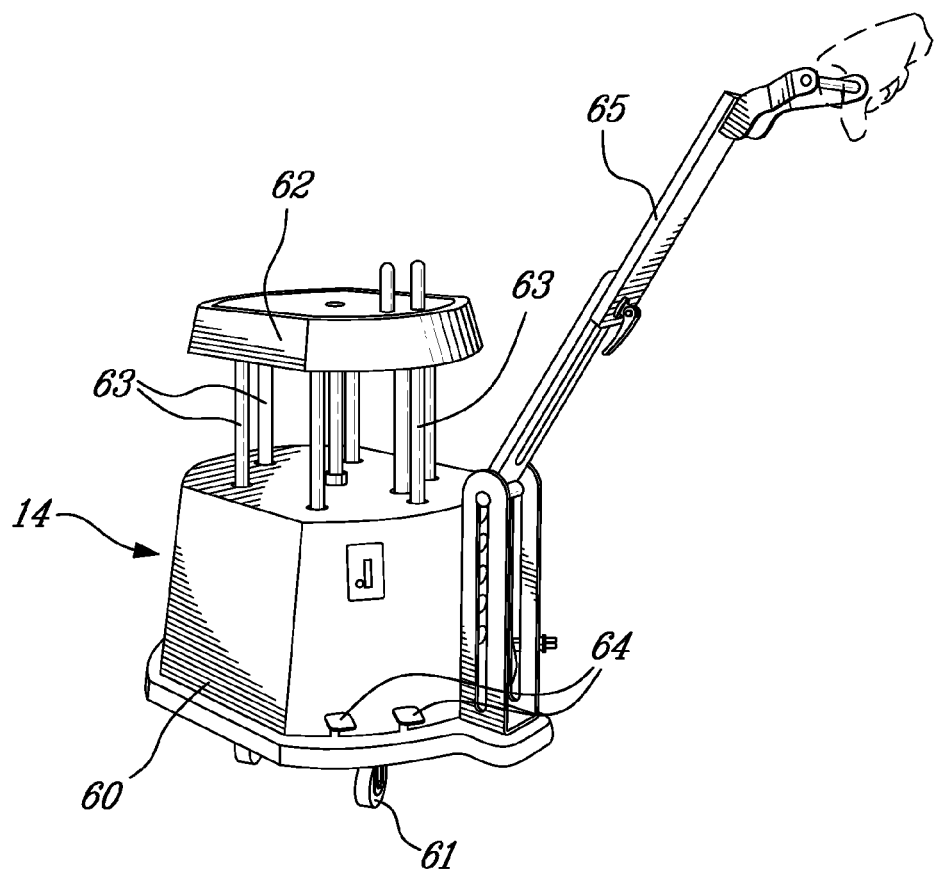
FIG. 7 is a perspective view of a wheeled stand of the medical support system of FIG. 1.

Referring to FIG. 1, the wheeled stand 14 is shown supporting the support frame 12. In FIG. 7, the wheeled stand 14 is shown free of the support frame 12. The wheeled stand 14 has a base 60 provided with swivel-type casters 61. A support platform 62 is supported by rods 63, which are the moveable portions of linear actuators actuated from the base 60.

Accordingly, by actuation of the linear actuators, the support platform 62 is displaceable vertically. Pedals 64 are provided to adjust the vertical position of the support platform 62.

In order to be used for the transportation of the support frame 12, the wheeled stand 14 is positioned under the support frame 12. The support platform 62 must be low enough so as to fit under the support frame 12. If the support platform 62 is too high, the pedals 64 are used to lower the support platform 62.

Once the wheeled stand 14 is in a suitable position under the support frame 12, the support platform 62 is raised using the pedals 64 to connect with the base plate 20 of the support frame 12. The support platform 62 may then be raised farther to lift the support frame 12 off the wall support 16. The support frame 12 is then displaceable as part of the medical support system 10. It is pointed out that the support frame 12 and wheeled stand 14 may be connected to a hospital bed, so as to be displaceable therewith.

In an embodiment, the linear actuators are electrically powered, and the base 60 encloses a rechargeable battery. It is contemplated to provide a back-up system to raise/lower the support platform 62, such as handle 65. The handle 65 is optionally connected to a manually-actuatable actuator raising/lowering the support platform 62. The handle 65 is used as well to pull/push the base 60.

Figure 8:
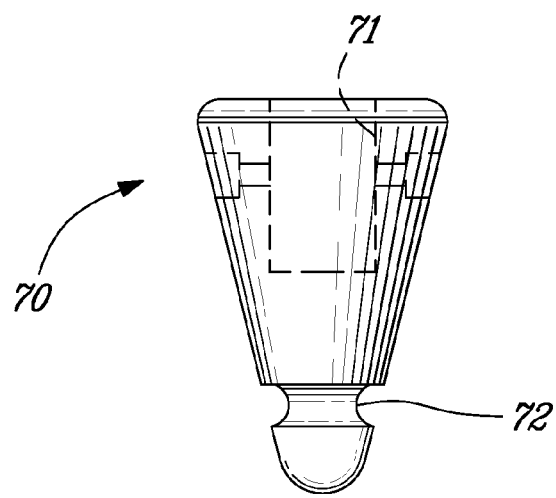
FIG. 8 is an elevation view of a support frame connector in accordance with another embodiment of the present application.

Referring to FIG. 8 a connector 70 is shown. The connector 70 is optionally used as an interface between the support frame 12 and the wheeled stand 14. More specifically, the connector 70 defines a cavity 71 that accommodates the bottom end of the main pole 21, with fasteners (not shown) being used to secure the connector 70 to the main pole 21. The connector 70 is generally shaped as an inverted cone, and will be received in a corresponding cavity in the support platform 62 of the wheeled stand 60. The shape of the connector 70 ensures that the main pipe 21 is centered in the platform 62, and that a suitable contact surface is provided therebetween.

A shoulder 72 is provided on the surface of the connector 70. The shoulder 72 cooperates with a locking system in the platform 62, to releasably lock the support frame 12 to the wheeled stand 14. The locking system features a blocking element (not shown) fitting into the shoulder 72 to prevent movement between the connector 70 and the platform 62.

The invention claimed is:

1. A support frame for supporting an intravenous bag and associated equipment, comprising:
    a main pole adapted to be secured to a structure so as to be self-standing, the main pole having a base at its bottom end, so as to be supported by the bottom end;
    a first pivotable pole adapted to support equipment associated with an intravenous bag;
    at least a first pivot joint between the main pole and the first pivotable pole such that the first pivotable pole rotates about the main pole;
    a second pivotable pole adapted to support equipment associated with an intravenous bag;
    at least a second pivot joint separate from the first pivot joint, between the main pole and the second pivotable pole such that the second pivotable pole rotates about the main pole independently from a rotation of the first pivotable pole about the main pole;
    a first rack supported by the first pivotable pole, the first rack being adapted to support an intravenous bag;
    a second rack supported by the second pivotable pole, the second rack being adapted to support an intravenous bag; and
    a wheeled stand having a wheeled base displaceable on a floor, and a support platform releasably connectable to the base of the main pole and vertically displaceable with respect to the wheeled base, so as to lift and release the main pole.

2. The support frame according to claim 1, wherein the first and the second pivot joint each have a pair of spaced-apart parallel arms pivotally connecting the respective pivotable poles to the main pole in a parallel relation.

3. The support frame according to claim 2, wherein the pivotable poles each define a support length portion between the parallel arms, the support length portion being adapted to support the equipment associated with the intravenous bag.

4. The support frame according to claim 3, wherein the support length portion has a length of up to 70 inches.

5. The support frame according to claim 1, wherein the first and the second pivot joint are releasably lockable so as to selectively block movement between the respective pivotable poles and the main pole.

6. The support frame according to claim 1, wherein a bottom end of the racks are concentrically received in a top end of the pivotable poles respectively, and further comprising a quick-coupling mechanism releasably locking the bottom end of the racks in the top end of the pivotable poles respectively, the quick-coupling mechanism having a collapsible sleeve about the bottom end of the racks, and a levered cam to manually collapse the sleeve.

7. The support frame according to claim 1, further comprising a spring within each of the pivotable poles, to bias the rack upwardly when the bottom end of the respective racks are accommodated in the respective pivotable poles.

8. The support frame according to claim 1, wherein each of the racks has at least one finger to support the intravenous bag, the at least one finger having a downwardly-oriented loop and a inward tip to hold the intravenous bag captive.

9. The support frame according to claim 8, wherein each of the racks has a horizontal portion to offset the fingers with respect to the respective pivotable pole.

10. The support frame according to claim 1, wherein the main pole has female connectors, adapted to be coupled to wall mounted male connectors.

11. The support frame according to claim 1, wherein the wheeled stand has a telescopic handle for being manually displaced on the ground.

\* \* \* \* \*